United States Patent [19]

Yamasaki et al.

[11] Patent Number: 4,497,930
[45] Date of Patent: Feb. 5, 1985

[54] PROCESS FOR PRODUCING HIGHLY WATER ABSORPTIVE POLYMER

[75] Inventors: Harumasa Yamasaki; Takatoshi Kobayashi; Yuzo Sumida, all of Wakayama, Japan

[73] Assignee: Kao Corporation, Tokyo, Japan

[21] Appl. No.: 527,134

[22] Filed: Aug. 26, 1983

[30] Foreign Application Priority Data

Sep. 2, 1982 [JP] Japan .............................. 57-153097
Jun. 20, 1983 [JP] Japan .............................. 58-110408
Jun. 20, 1983 [JP] Japan .............................. 58-110409

[51] Int. Cl.$^3$ ...................... C08L 33/00; C08L 33/08
[52] U.S. Cl. ............................. 524/556; 525/54.24; 526/238.22; 526/328; 604/372
[58] Field of Search ............... 524/556; 525/7–7.4, 525/54.24; 526/238.22, 328

[56] References Cited

U.S. PATENT DOCUMENTS 3,847,851 11/1974 Tugukuni et al. ............... 523/202
3,929,741 12/1975 Laskey .............................. 526/288
4,059,552 11/1977 Zweigle et al. .................... 526/306
4,093,776 6/1978 Aoki et al. ........................ 526/207
4,135,943 1/1979 Morishita et al. ................ 106/209
4,179,367 12/1979 Barthell et al. ................... 524/556
4,367,323 1/1983 Kitamura et al. ................. 526/317

Primary Examiner—Ronald W. Griffin
Attorney, Agent, or Firm—Flynn, Thiel, Boutell & Tanis

[57] ABSTRACT

A highly water absorbent polymer having high resistance to salt solution is prepared by crosslinking a hyrophilic polymer or copolymer having carboxyl and/or carboxylate groups and water content of 10 to 40 wt. % with a crosslinking agent having at least two functional groups capable of reaction with said carboxyl and carboxylate group. An improved hydrophilic polymer is produced by polymerizing a monomer with a persulfate and a hydroperoxide as combined initiators. Another improved hydrophilic polymer is prepared by polymerizing a monomer with a persulfate and adding a hydroperoxide to the resulting polymer.

11 Claims, No Drawings

PROCESS FOR PRODUCING HIGHLY WATER ABSORPTIVE POLYMER

This invention relates to a process for producing a highly water absorptive polymer, or absorbent polymer. More particularly, the present invention relates to a process for producing a water absorbing material having excellent salt resistance and a high water absorption rate.

Various water absorbing materials such as paper, pulp, sponge or the like have been used conventionally as sanitary materials (such as sanitary napkins and paper diapers) and in the agricultural field. In addition to the low water absorbing capacity, they involve the problem that the water that has been absorbed is mostly squeezed out again if pressure is applied to them.

Water absorbing materials such as hydrolyzed starch-acrylonitrile graft copolymer, modified cellulose ether, or hydrolyzed methyl acrylatevinyl acetate copolymer have been proposed and improved recently as the materials that are substitutes for the water absorbing materials described above. However, these materials can not always exhibit excellent water absorbing capacity nor high water absorption rate, and really satisfactory water absorbing materials have not been obtained yet.

The inventors of the present invention proposed already a water absorbing material having an excellent water absorbing property (Japanese Patent Publication No. 30710/1979), and a further improved water absorbing material (Japanese Patent Application Nos. 43488/1981 and 43489/1981). However, the materials disclosed in these prior art inventions involved the problem that since they consist of a macro-molecular electrolyte, the performance in a salt solution drops remarkably. Accordingly, early development of water absorbing materials having high salt resistance has been eagerly desired.

The inventors of the present invention have carried out intensive studies to obtain super water absorbent polymers having an excellent salt resistance and a high water absorption rate but which are free of the problem described above, and have found that a polymer having excellent water absorbing properties, especially an excellent salt resistance and a high water absorption rate, can be obtained by adding a crosslinking agent to a hydrophilic polymer while the water content of the hydrous polymer is adjusted within a specified range, and then crosslinking the polymer. The present invention has been completed on the basis of this finding.

In other words, the present invention provides a process for producing a highly water-absorbent polymer which is characterized in that a hydrous hydrophilic polymer which has carboxyl groups (or carboxylate groups) and whose water content is adjusted to 10 to 40 wt% is crosslinked by a cross-linking agent having at least two functional groups capable of reacting with the carboxyl group (or the carboxylate group).

Conventional processes for preparing water absorbent polymers primarily comprise crosslinking a water-soluble polymer to some extent so as to make the polymer water-insoluble. The following two methods have been proposed as the crosslinking method:
(1) to effect self-crosslinkage by optimizing the production condition, and
(2) to add a crosslinking agent during, or after, polymerization to cause crosslinking.

Though the resulting water absorbent polymers have excellent properties, none of them can satisfy all the requirements listed below.

Performances required for a water absorbing polymer are (1) water absorbent capacity, (2) water absorption rate and (3) gel strength and the following correlation is found generally between these requirements:

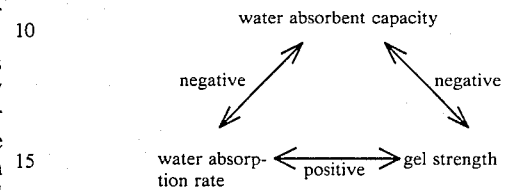

Conventional water absorbing polymers in general are based upon the balance of these requirements whereby each performance is sacrificed to some extent.

The process of the present invention can however eliminate this drawback and can produce an epoch-making highly water-absorbent polymer which can satisfy all these requirements.

The important requirement in accomplishing the object of the present invention is that a hydrophilic polymer contains carboxyl groups (or carboxylate groups) and the water content of the hydrous polymer prepared therefrom is adjusted within a specified range.

Any polymers can be used as the hydrophilic polymer of the present invention without any limitation to their kind and to the process for producing them so long as they have a carboxyl group (or a carboxylate group) as their structural unit.

Examples of the hydrophilic polymers that can be used suitably in the present invention are polysodium acrylate prepared by reversed phase suspension polymerization disclosed in Japanese Patent Publication No. 30710/1979 and Japanese Patent Laid-Open No. 26909/1981, polysodium acrylate prepared by aqueous solution polymerization (adiabatic polymerization, membrane polymerization) disclosed in Japanese Patent Laid-Open No. 133413/1980, and starch-sodium acrylate graft copolymer disclosed in Japanese Patent Publication No. 46199/1978. In producing these polymers, addition of a trace amount of crosslinking agent does not impede the effect of the present invention. It is preferred further that these polymers be self-crosslinked. It is one of the essential requirements in the present invention that the water content of the hydrous polymer is adjusted, and so that a dehydration step is generally necessary after the synthesis of the polymer. For this reason, polymers prepared by the reversed phase suspension polymerization process are generally preferred from the aspect of workability and the like. Examples of the polymer having carboxyl groups (or carboxylate groups) are generally polyacrylic acid (and its salts) and polymethacrylic acid (and its salts), and they can be used suitably in the process of the present invention. It is also possible to use copolymers prepared by copolymerizing acrylic or methacrylic acid with comonomers such as maleic acid, itaconic acid, acrylamide, 2-acrylamido-2-methylpropanesulfonic acid, 2-(meth)acryloylethanesulfonic acid, or 2-hydroxyethyl(meth)acrylate within a range where the performance of the highly water absorbent polymer of the present invention is not reduced.

According to the invention, the above mentioned, conventional hydrophilic polymer is used. In addition, the inventors have found that the following two hydrophilic polymers can improve the advantageous effects of the invention.

The first hydrophilic polymer is prepared by polymerizing or copolymerizing a polymerizable monomer having a carboxyl group and/or carboxylate group in the presence of a persulfate and a hydroperoxide as combined polymerization initiators. After this hydrophilic polymer has been adjusted to have a water content of 10 to 40 wt. %, it is crosslinked with a crosslinking agent.

Acrylic acid, a salt thereof, methacrylic acid and a salt thereof are used as a monomer having a carboxyl and/or carboxylate group. As a comonomer, the above listed ones are used.

The adjustment of a water content of the obtained hydrophilic polymer is carried out by the azeotropic dehydration, mere drying and other conventional methods.

In order to obtain the first hydrophilic polymer, there is no limitation to polymerization methods except for the following. It is essential that the water content of the resulting hydrophilic polymer be adjusted within the specified range described above so that dehydration is generally necessary after the synthesis of the polymer. For this reason, reversed phase suspension polymerization is preferred from the aspect of workability.

It is also essential for production of the first polymer that a persulfate and a hydroperoxide are used in combination as polymerization initiators. The inventors of the present invention proposed previously a method of obtaining a highly water absorbent polymer by use of two kinds of polymerization initiators in the polymerization (Japanese Patent Laid-Open No. 161408/1981), but the polymer obtained by this method has a low water absorption rate, though it is highly water absorptive, and has a critical drawback that it can not be used practically as sanitary materials such as sanitary napkins and paper diapers. In accordance with the present invention, however, the resulting hydrophilic polymer is crosslinked under a specified reaction condition as described above, so that a polymer having a highly water absorbing property as well as a high water absorption rate can be obtained and the problem with the prior art described above can thus be solved.

Examples of the persulfate to be used in the present invention are sodium persulfate, potassium persulfate, and ammonium persulfate. Examples of the hydroperoxide are hydrogen peroxide, t-butyl hydroperoxide, and cumenehydroperoxide. The amount of the initiator is preferably 0.01 to 1 wt% for the persulfate and 0.01 to 2 wt% for the hydroperoxide, and they can be used in an arbitrary combination.

A second hydrophilic polymer is prepared by polymerizing or copolymerizing a polymerizable monomer having a carboxyl group or/and a carboxylate group using a persulfate as a polymerization initiator, adding a hydroperoxide to the resulting polymer, adjusting the water content of the polymer to 10 to 40% by weight and thereafter crosslinking the polymer using a crosslinking agent.

In order to prepare the second polymer, it is essential that a monomer is polymerized with a persulfate as a polymerization initiator; a hydroperoxide is added to the polymer mixture; and a water content is adjusted within the above defined range.

It is preferably that the persulfate is used in an amount of 0.01 to 1 wt. % per the monomer used and the hydroperoxide is used in an amount of 0.005 to 2 wt. %, especially from 0.01 to 2 wt. %, per the monomer used. It is suitable that the aging time after addition of a hydroperoxide to the polymerization mixture is 30 minutes or longer.

When the reverse phase suspension polymerization method is employed in order to produce the first and second polymers, a protective colloid may be used during the polymerization step. It includes a sorbitan fatty acid ester such as sorbitan monostearate and sorbitan monolaurate. A high molecular weight dispersant may be used, including cellulose ethers such as ethylcellulose, benzylcellulose and ethylhydroxyethylcellulose, cellulose esters such as cellulose acetate, cellulose butyrate and cellulose acetatebutyrate, maleinized polybutadiene, maleinized polyethylene and maleinized alpha-olefins.

The water content of the hydrous hydrophilic polymer is of particular importance in the process of the present invention when a crosslinking agent is added to effect the crosslinking reaction. A process for producing a water absorbing polymer by causing the crosslinking reaction after the polymerization is known in the art. For example, Japanese Patent Laid-Open No. 131608/1981 discloses a process in which polyacrylate is crosslinked in a mixture solvent consisting of water and a hydrophilic organic solvent, and Japanese Patent Publication No. 28505/1982 discloses a process in which polyacrylic acid (or its salt) is crosslinked in the presence of water.

However, the water content of these hydrous polymers is at least 50% by weight and, especially in the latter case, it is at least 70% by weight. The effect of the present invention can not be obtained if the polymers have such a high water content.

Generally, hydrophilic polymers can be obtained by carrying out the polymerization in an aqueous solution having a monomer concentration of up to 45% by weight, that is, a water content of at least 55% by weight. In practising the present invention, therefore, it is necessary to control the water content of hydrophilic polymers obtained by an ordinary process.

In accordance with the present invention, the water content must be essentially in the range of 10 to 40% by weight (on the basis of the total amount of the hydrous hydrophilic polymer) and, more particularly, from 15 to 35% by weight (on the basis of the total amount). If the water content of the hydrophilic polymer is out of the range described above, the remarkable effect of the present invention can not be obtained because the water absorbent capacity and/or the water absorption rate will be lowered. The object of the present invention can be accomplished, for example, by concentrating an acrylate polymer obtained by the reversed phase suspension polymerization process, so that the water content is within the range described above.

Any crosslinking agents can be used in the present invention so long as they have at least two functional groups that can react with the carboxyl group (or the carboxylate group). Examples of the crosslinking agent are polyglycidyl ethers such as ethylene glycol diglycidyl ether, polyethylene glycol diglycidyl ether, or glycerol triglycidyl ether; haloepoxy compounds such as epichlorohydrine or α-methylchlorohydrin; polyaldehydes such as glutaraldehyde or glyoxal; polyols such as glycerol, pentaerythritol or ethylene glycol; and polyamines such as ethylenediamine. Among them, polyglycidyl ethers such as ethylene glycol diglycidyl ether are preferred.

The amount of the crosslinking agent varies depending upon the kind of the crosslinking agent itself and upon the kind of the polymer, but is generally from 0.01 to 5.0% by weight on the basis of the polymer. If the amount of the crosslinking agent is below 0.01% by weight, the effect of the addition can not be sufficiently exhibited while if it is above 5% by weight, the crosslinking density becomes high and the water absorbent capacity will drop contrary to the intention of the present invention.

Various methods may be employed in order to add the crosslinking agent and to cause the crosslinking reaction. In the case of a polymer which is prepared by the reversed phase suspension polymerization process, the crosslinking agent is added while the hydrophilic polymer, whose water content is adjusted within the range specified in the present invention, is suspended in an organic solvent, and heat-treatment is carried out. When the hydrophilic polymer is prepared by the membrane polymerization or the like, the resulting polymer gel is milled and, after the water content is adjusted by drying, the milled polymer is placed in a kneader, whereupon the crosslinking agent is added and heat-treatment is carried out to effect the crosslinking reaction. To smoothly carry out the crosslinking reaction, heating is preferably made and the reaction is carried out preferably at a temperature ranging from 40° to 150° C.

Water absorbing materials having an excellent salt resistance and a high water absorption rate can be obtained in accordance with the present invention. They can be used advantageously as water-retaining materials for agricultural use and water-absorbing materials for sanitary materials. The highly water absorptive polymer obtained by the process of the present invention can be applied advantageously to paper napkins which must rapidly absorb large quantities of urine and to sanitary napkins which must absorb the blood, and they can eliminate leak and offensive feel.

The present invention will now be described with reference to Examples thereof and to Comparative Examples, but these Examples do not limit the present invention, in particular.

In Examples and Comparative Examples which follow, the water absorbent capacity is determined in the following manner. About 1 g of the polymer is dispersed in a large excess of ion-exchanged water or a physiological saline solution to effect swelling and is then filtered using an 80 mesh net. The weight (W) of the swollen polymer is measured and this value is divided by the initial polymer weight ($W_o$).

In other words, the water absorbent capacity (g/g) is defined as $W/W_o$. The water absorption rate is expressed in terms of the quantity of the physiological saline solution absorbed by 0.3 g of the polymer within 10 minutes.

EXAMPLES 1 TO 3

230 ml of cyclohexane and 1.8 g of sorbitan monostearate were charged in a 500 ml four-necked round-bottomed flask equipped with a stirrer, a reflux condenser, a dropping funnel and a nitrogen gas inlet pipe, and were heated to 75° C. Separately, 30 g of acrylic acid was neutralized by 13.4 g of caustic soda dissolved in 39 g of water in an Erlenmeyer flask. The monomer concentration in the aqueous monomer solution was 45% (water content: 55%). Next, 0.1 g of potassium persulfate was dissolved in this solution. The resulting monomer solution was fed dropwise to the four-necked flask in a nitrogen atmosphere in the course of 1.5 hours to effect polymerization, and was then held at 70° to 75° C. for 0.5 hour to complete the polymerization. Thereafter, the water content of the polymer suspended in cyclohexane was adjusted to 35%, 27% and 20%, respectively, by azeotropic dehydration (while refluxing cyclohexane). Then, an aqueous solution prepared by dissolving 0.03 g of ethylene glycol diglycidyl ether in 1 ml of water was added to each of the polymers at 73° C., and each solution was further held at that temperature for 2 hours. Cyclohexane was then removed and each polymer was dried under a reduced pressure at 80° to 100° C., providing a water absorbent polymer.

EXAMPLE 4

Polymerization was carried out in the same way as in Example 1 except that 0.5 g of ethylcellulose T-50 was used in place of sorbitan monostearate. After the polymerization was completed, the water content of the polymer was adjusted to 22%. After an aqueous solution prepared by dissolving 0.04 g of glycerol diglycidyl ether in 1 ml of water was added at 73° C., the polymer solution was held at that temperature for 3 hours. Cyclohexane was then removed and the polymer was dried under a reduced pressure and at 80° to 100° C., providing a water absorbent polymer.

EXAMPLE 5

Polymerization was carried out in the same way as in Example 4 except that the monomer concentration in the aqueous monomer solution was 35% and 0.003 g of N,N'-methylenebisacrylamide was further added. The water content of the polymer was controlled to 27% by azeotropic dehydration after the polymerization, and an aqueous solution prepared by dissolving 0.15 g of polyethylene glycol diglycidyl ether (n=9) was added at 60° C. The polymer solution was held at this temperature for 3 hours and cyclohexane was then removed. The polymer was dried under a reduced pressure at 80° to 110° C., providing a water absorbent polymer.

EXAMPLE 6

30 g of acrylic acid was neutralized by 13.4 g of caustic soda dissolved in 39 g of water. The monomer concentration in the aqueous monomer solution was 45%. Next, 0.1 g of sodium persulfate was dissolved in this solution. The resulting monomer solution was caused to flow between two Teflon plates and was polymerized while being kept in the film form at 65° C. for 3 hours. The resulting polymer gel was cut in 3 mm-slices and the slices were dried by a hot-air dryer until the water content became 30%. The dried slices were placed in a kneader and an aqueous solution prepared by dissolving 0.03 g of ethylene glycol diglycidyl ether in 1 ml of water was sprayed. After the polymer slices were held at 70° C. for 1 hour, they were dried under a reduced pressure at 70° to 80° C. The resulting polymer was milled to provide a water absorbent polymer having a median particle size ranging from 100 to 250 μm.

COMPARATIVE EXAMPLE 1

Polymerization was carried out in the same way as in Example 1 except that 0.03 g of ethylene glycol diglycidyl ether was added to the aqueous monomer solution and the crosslinking reaction was carried out simultaneously with the polymerization. After the polymerization was completed, cyclohexane was removed and the polymer was dried under a reduced pressure at 80° to 100° C., providing a water absorbent polymer.

COMPARATIVE EXAMPLE 2

Polymerization was carried out in the same way as in Example 1 except that an aqueous solution prepared by dissolving 0.03 g of ethylene glycol diglycidyl ether in 1 ml of water was added after completion of the polymerization (the water content of the hydrous polymer was 55%) and the mixture was held at 73° C. for 1 hour. After the crosslinking reaction was completed, cyclohexane was removed and the polymer was dried under a reduced pressure at 80° to 100° C., providing a water absorbent polymer.

COMPARATIVE EXAMPLE 3

Polymerization was carried out in the same way as in Example 1 except that an aqueous solution prepared by dissolving 0.03 g of ethylene glycol diglycidyl ether in 1 ml of water was added at the point when the water content of the polymer was controlled to 45% by azeotropic dehydration, and the polymer solution was held at 60° C. for 2 hours. After the crosslinking reaction was completed, cyclohexane was removed and the polymer was dried under a reduced pressure at 80° to 100° C., providing a water absorbent polymer.

COMPARATIVE EXAMPLE 4

After polymerization was carried out in the same way as in Example 1, cyclohexane was removed and the polymer was dried under a reduced pressure at 70° to 80° C. The water content of this polymer was 7%. While this polymer was again dispersed and suspended in cyclohexane, an aqueous solution prepared by dissolving 0.03 g of ethylene glycol diglycidyl ether in 1 ml of water was added, and the polymer suspension was held at 70° C. for 1 hour. Thereafter, cyclohexane was removed and the polymer was dried under a reduced pressure at 80° to 100° C., providing a water absorbing polymer.

The water absorbent capacity and water absorption rate of the polymer obtained in each of Examples 1 to 6 and Comparative Examples 1 to 4 are shown in Table 1.

TABLE 1

| No. | | Water absorbent capacity (g/g) | | Water absorption rate (ml) |
| --- | --- | --- | --- | --- |
| | | Ion-exchanged water | Physiological saline solution | |
| Example | 1 | 510 | 72 | 25.6 |
| | 2 | 600 | 73 | 27.3 |
| | 3 | 750 | 85 | 28.4 |
| | 4 | 620 | 80 | 28.0 |
| | 5 | 530 | 73 | 25.9 |
| | 6 | 450 | 70 | 24.0 |
| Comparative example | 1 | 400 | 50 | 12.3 |
| | 2 | 410 | 49 | 11.4 |
| | 3 | 435 | 51 | 10.1 |
| | 4 | 550 | 60 | 10.5 |

It can be seen clearly from Table 1 that the polymers of the present invention have an excellent salt resistance and a high water absorption rate.

EXAMPLES 7 TO 9

230 ml of cyclohexane and 1.0 g of ethylcellulose N-100 were charged in a 500-ml four-necked round-bottomed flask equipped with a stirrer, a reflux condenser, a dropping funnel and a nitrogen gas inlet pipe, and were heated to 75° C. Separately, 30 g of acrylic acid was neutralized by 52.4 g of a 25.6 wt.% aqueous caustic soda solution in an Erlenmeyer flask. The monomer concentration in the aqueous monomer solution was 45% (water content: 55%). Next, 0.1 g of potassium persulfate and 0.06 g, 0.1 g and 0.18 g of 30 wt.% aqueous hydrogen peroxide were dissolved in the monomer solution, respectively. Each monomer solution was fed dropwise to the four-necked flask in the course of 1.5 hours at 70° to 75° C. in the nitrogen atmosphere to effect polymerization. Thereafter, the water content of the polymer suspended in cyclohexane was adjusted to 25 wt%, 20 wt% and 15 wt% by azeotropic dehydration. An aqueous solution prepared by dissolving 0.02 g of ethylene glycol diglycidyl ether in 1 ml of water was added to each polymer at 73° C. and was then held at this temperature for 2 hours. Cyclohexane was removed and the polymers were dried under a reduced pressure at 80° to 100° C., providing water absorbent polymers, respectively.

EXAMPLE 10

Polymerization was carried out in the same way as in Example 7 except that 1.8 g of maleic acid-modified polyethylene wax ("Hi-wax 1105-A", a product of Mitsui Petrochemical Co., molecular weight of 1,400, density of 0.94 and acid value of 60) was used in place of ethylcellulose N-100 and 0.2 g of 70 wt% t-butyl hydroperoxide was used in place of hydrogen peroxide. After the polymerization was completed and the water content of the polymer was controlled to 20% by weight by azeotropic dehydration, and an aqueous solution prepared by dissolving 0.03 g of glycerol diglycidyl ether in 1 ml of water was added at 73° C. The polymer solution was held at this temperature for 3 hours and then cyclohexane was removed. The polymer was dried under a reduced pressure at 80° to 100° C., providing a water absorbent polymer.

EXAMPLE 11

The same procedures as in Example 7 were followed to obtain a water absorbing polymer except that the monomer concentration in the aqueous solution in the feeding method of Example 7 was changed to 35 wt% and 0.003 g of N,N'-methylenebisacrylamide was further added.

EXAMPLE 12

The same procedures as in Example 7 were followed to obtain a water absorbing polymer except that the solvent in the feeding method of Example 7 was changed to n-hexane and 1.8 g of sorbitan monostearate was used in place of ethylcellulose N-100.

EXAMPLE 13

30 g of acrylic acid was neutralized by 13.4 g of caustic soda dissolved in 39 g of water, and the monomer concentration in an aqueous monomer solution became 45 wt%. Further, 0.1 g of sodium persulfate and 0.03 g of 30 wt% hydrogen peroxide were dissolved in this solution. The resulting monomer solution was caused to flow between two Teflon plates in the form of a film and was held at 65° C. for 3 hours to effect polymerization. After the resulting polymer gel was cut in 2-mm slices, the polymer slices were dried by a hot air dryer until the water content became 28 wt%. The polymer was placed in a kneader and an aqueous solution prepared by dissolving 0.03 g of ethylene glycol diglycidyl ether in 1 ml of water was sprayed. After the polymer was held at 70° C. for 1 hour, the polymer was dried under a reduced pressure at 70° to 80° C. The resulting polymer was milled to provide a water absorbent polymer having a medium particle diameter ranging from 100 to 250 μm.

TABLE 2

|  |  | Water absorbent capacity (g/g) | Water absorption rate (ml) |
|---|---|---|---|
| Example | 7 | 84 | 19.8 |
|  | 8 | 91 | 22.1 |
|  | 9 | 102 | 20.3 |
|  | 10 | 89 | 20.7 |
|  | 11 | 82 | 18.8 |
|  | 12 | 85 | 20.5 |
|  | 13 | 83 | 18.2 |

EXAMPLES 14 TO 16

230 ml of cyclohexane and 1.0 g of ethylcellulose N-100 were charged in a 500 ml four-necked round-bottomed flask equipped with a stirrer, a reflux condenser, a dropping funnel and a nitrogen gas inlet pipe, and were heated to 75° C. Separately, 30 g of acrylic acid was neutralized by 52.4 g of a 25.6% aqueous caustic soda solution in an Erlenmeyer flask. The monomer concentration in the aqueous monomer solution was 45% (water content: 55%). Next, 0.1 g of potassium persulfate was dissolved in the monomer solution. The resulting monomer solution was fed dropwise to the four-necked flask in the course of one hour at 70° to 75° C. in the nitrogen atmosphere to effect polymerization. After the polymerization was completed, 0.07 g, 0.14 g and 0.21 g of 35% hydrogen peroxide were added, respectively, and each solution was held for 1 hour. Thereafter, the water content of each solution was adjusted to 20% by weight by azeotropic dehydration. An aqueous solution prepared by dissolving 0.02 g of ethylene glycol diglycidyl ether in 1 ml of water was added at 73° C. and was then held at this temperature for 2 hours. Cyclohexane was removed and the polymers were dried under a reduced pressure at 80° to 100° C., providing water absorbent polymers, respectively.

EXAMPLE 17

Polymerization was carried out in the same way as in Example 14 except that 1.8 g of maleic acid-modified polyethylene wax ("Hi-wax 1105-A", a product of Mitsui Petrochemical Co., molecular weight of 1,400, density of 0.94 and acid value of 60) was used in place of ethylcellulose N-100 and 0.2 g of 70 wt% t-butyl hydroperoxide was used in place of hydrogen peroxide. After t-butyl hydroperoxide was added and aged, the water content of the polymer was controlled to 15% by weight by azeotropic dehydration, and an aqueous solution prepared by dissolving 0.03 g of glycerol diglycidyl ether in 1 ml of water was added at 73° C. The polymer solution was held at this temperature for 3 hours and then cyclohexane was removed. The polymer was dried under a reduced pressure at 80° to 100° C., providing a water absorbing polymer.

EXAMPLE 18

Polymerization was carried out in the same way as in Example 14 except that n-hexane was used in place of cyclohexane and 1.8 g of sorbitan monostearate was used in place of ethylcellulose N-100. Thus, a water absorbent polymer was obtained in the same way as in Example 14.

The water absorbent capacity and water absorption rate of the polymers obtained in Examples 14 to 18 are illustrated in Table 3 below.

TABLE 3

|  |  | Water absorbent capacity (g/g) | Water absorption rate (ml) |
|---|---|---|---|
| Example | 14 | 84 | 18.3 |
|  | 15 | 90 | 20.3 |
|  | 16 | 95 | 20.6 |
|  | 17 | 87 | 18.8 |
|  | 18 | 83 | 18.2 |

The embodiments of the invention in which an exclusive property or privilege is claimed are defined as follows:

1. A process for producing a highly water absorbent polymer, which comprises:
   polymerizing a hydrophilic, carboxylic acid monomer or salt thereof, which monomer is dissolved in water, to obtain a hydrous hydrophilic polymer;
   then dehydrating said hydrous hydrophilic polymer until the water content thereof is from 10 to 40 wt.%, based on the total amount of said hydrous hydrophilic polymer,
   then adding to said hydrous hydrophilic polymer an effective amount of a crosslinking agent having at least two functional groups in the molecule, which functional groups are capable of reacting with carboxyl and carboxylate groups, and effecting crosslinking of said hydrous hydrophilic polymer.

2. A process as claimed in claim 1 in which, in said dehydrating step, the water content of said polymer is reduced to 15 to 35 wt.%.

3. A process as claimed in claim 1 in which said crosslinking agent is selected from the group consisting of polyglycidyl ethers, haloepoxy compounds, polyaldehydes and polyamines.

4. A process as claimed in claim 1 in which said crosslinking agent is a polyglycidyl ether.

5. A process as claimed in claim 1 in which, in said polymerizing step, said monomer is polymerized in the presence of both a persulfate polymerization initiator and a hydroperoxide polymerization initiator, the amount of said persulfate polymerization initiator being in the range of from 0.01 to 1.0 wt.%, based on the weight of said monomer, and the amount of said hydroperoxide initiator being in the range of from 0.01 to 2.0 wt.%, based on the weight of said monomer.

6. A process as claimed in claim 1 in which, in said polymerizing step, said monomer is polymerized in the presence of from 0.01 to 1.0 wt.%, based on the weight of said monomer, of a persulfate polymerization initiator, and thereafter but prior to said dehydrating step, adding to said polymer from 0.005 to 2.0 wt.%, based on the weight of said monomer, of a hydroperoxide polymerization initiator and then aging the polymerization mixture before performing said dehydrating step.

7. A process as claimed in claim 1 in which said polymerizing step is reversed phase suspension polymerization wherein droplets of the solution of the monomer in water are suspended in an oil medium.

8. A process as claimed in claim 1 in which the amount of said crosslinking agent is from 0.01 to 5 wt.%, based on the weight of said hydrous hydrophilic polymer.

9. A process as claimed in claim 1, claim 5 or claim 6 in which said monomer is selected from the group consisting of acrylic acid, methacrylic acid and alkali metal salts of said acids.

10. A process as claimed in claim 1, claim 5 or claim 6 in which said monomer is sodium acrylate and said crosslinking agent is selected from the group consisting of ethylene glycol diglycidyl ether, polyethylene glycol diglycidyl ether and glycerol diglycidyl ether.

11. A process as claimed in claim 1, claim 5 or claim 6 in which in said crosslinking step, the mixture of said hydrous hydrophilic polymer and said crosslinking agent is heated to a temperature of 40° to 150° C.

* * * * *